United States Patent
Sakamoto et al.

(10) Patent No.: US 10,328,417 B2
(45) Date of Patent: Jun. 25, 2019

(54) CATALYST MIXTURE FOR OLEFIN METATHESIS REACTIONS, METHOD OF PRODUCING SAME, AND METHOD OF PRODUCING PROPYLENE USING SAME

(71) Applicant: Clariant Catalysts (Japan) K.K., Tokyo (JP)

(72) Inventors: Yuzuru Sakamoto, Toyama (JP); Moriyasu Sugeta, Toyama (JP)

(73) Assignee: Clariant Catalysts (Japan) K.K., Tokyo (JP)

( * ) Notice: Subject to any disclaimer, the term of this patent is extended or adjusted under 35 U.S.C. 154(b) by 239 days.

(21) Appl. No.: 14/433,513

(22) PCT Filed: Oct. 6, 2012

(86) PCT No.: PCT/JP2012/076053
§ 371 (c)(1),
(2) Date: Apr. 3, 2015

(87) PCT Pub. No.: WO2014/054185
PCT Pub. Date: Apr. 10, 2014

(65) Prior Publication Data
US 2015/0273439 A1    Oct. 1, 2015

(51) Int. Cl.
*B01J 23/58* (2006.01)
*B01J 23/30* (2006.01)
*C07C 6/04* (2006.01)
*B01J 23/04* (2006.01)
*B01J 35/00* (2006.01)
*B01J 37/02* (2006.01)
*B01J 37/04* (2006.01)
*B01J 37/08* (2006.01)

(52) U.S. Cl.
CPC .............. *B01J 23/30* (2013.01); *B01J 23/04* (2013.01); *B01J 35/0006* (2013.01); *B01J 37/0201* (2013.01); *B01J 37/04* (2013.01); *B01J 37/08* (2013.01); *C07C 6/04* (2013.01); *C07C 2521/08* (2013.01); *C07C 2523/02* (2013.01); *C07C 2523/04* (2013.01); *C07C 2523/30* (2013.01); *Y02P 20/52* (2015.11)

(58) Field of Classification Search
None
See application file for complete search history.

(56) References Cited

U.S. PATENT DOCUMENTS

| | | |
|---|---|---|
| 4,575,575 A | 3/1986 | Drake et al. |
| 4,684,760 A | 8/1987 | Drake |
| 4,754,098 A | 6/1988 | Drake |
| 2005/0124839 A1 | 6/2005 | Gartside et al. |
| 2010/0056839 A1* | 3/2010 | Ramachandran ...... B01J 23/007 585/646 |
| 2010/0063339 A1 | 3/2010 | Takai et al. |
| 2010/0145126 A1 | 6/2010 | Takai et al. |
| 2010/0167911 A1 | 7/2010 | Shum |
| 2011/0021858 A1 | 1/2011 | Ramachandran |
| 2011/0077444 A1 | 3/2011 | Butler |
| 2014/0081061 A1* | 3/2014 | Stanley ................. C07C 5/2512 585/314 |
| 2015/0141593 A1* | 5/2015 | Yang ................... C08F 4/65912 526/118 |
| 2015/0141605 A1* | 5/2015 | Bradin ...................... C07C 1/20 526/268 |
| 2015/0273439 A1* | 10/2015 | Sakamoto ............... B01J 37/08 585/644 |

FOREIGN PATENT DOCUMENTS

| | | | |
|---|---|---|---|
| EP | 2330091 | | 6/2011 |
| JP | 62-197147 A | | 8/1987 |
| JP | WO2006093058 | * | 8/2006 |
| JP | 2008-519033 A | | 6/2008 |
| JP | 2012-502057 A | | 6/2012 |
| JP | 2012-513895 A | | 6/2012 |

(Continued)

OTHER PUBLICATIONS

Robert L. Banks et al., New developments and concepts in enhancing activities of heterogeneous metathesis catalysts, Journal of Molecular Catalysis, 1985, vol. 28, pp. 117-131.
International Search Report of PCT application PCT/JP2012/076053 dated Nov. 13, 2012.
Korean Intellectual Property Office Search Report Application No. UAE/P/0440/2015 pp. 1-11.
Supplementary European Search Report, International application No. EP 12886117, International filing date Oct. 6, 2015, dated Jul. 6, 2016.

(Continued)

*Primary Examiner* — Melvin C. Mayes
*Assistant Examiner* — Colette B Nguyen
(74) *Attorney, Agent, or Firm* — Bond, Schoeneck & King, PLLC; Joseph Noto

(57) ABSTRACT

Provided is mixed catalysts for an olefin metathesis reaction having a high selectivity so that side reactions do not take place and having a high activity, which side reactions are polymerization reactions, isomerization from 2-butene to 1-butene, and reactions of 1-butene with other molecules. Mixed catalysts for an olefin metathesis reaction can be provided, the mixed catalyst comprising a metathesis catalyst which is tungsten oxide supported on a silica carrier and a co-catalyst that is composited from at least three oxides of Groups 1 and 2 metallic elements. By using the catalyst an olefin metathesis reaction of generating propylene from ethylene and 2-butene, the solid basicity to promote the metathesis reaction can be increase, and influences of gas containing isomers of 2-butene contained in raw material gas can be inhibited to increase the production efficiency of propylene even at low temperatures.

4 Claims, 1 Drawing Sheet

(56) References Cited

FOREIGN PATENT DOCUMENTS

| JP | 2012-520348 A | 9/2012 |
| WO | WO2006/093058 A1 | 9/2006 |
| WO | WO2008/136280 A1 | 11/2008 |
| WO | WO2010/024319 A1 | 3/2010 |

OTHER PUBLICATIONS

Pearce et al. "Catalysis and Chemical Process". Chengdu University of Science and Technology Press. Mar. 31, 1990.
JP100052, Office Action dated Nov. 1, 2016.

* cited by examiner

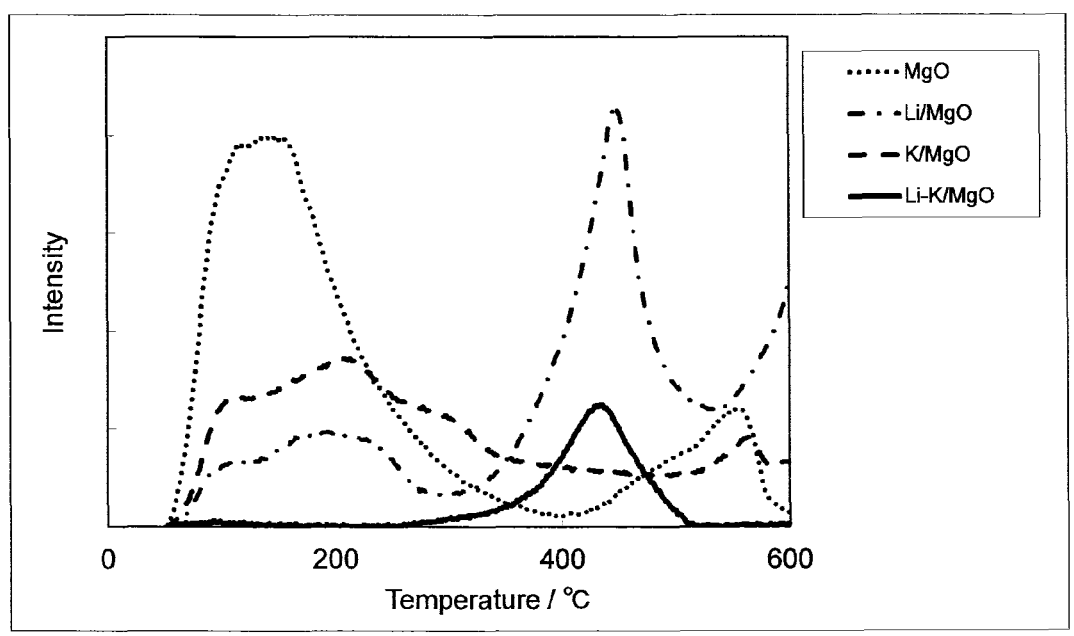

CATALYST MIXTURE FOR OLEFIN METATHESIS REACTIONS, METHOD OF PRODUCING SAME, AND METHOD OF PRODUCING PROPYLENE USING SAME

BACKGROUND OF THE INVENTION

Field of the Invention

The present invention relates to catalysts for an olefin metathesis reaction used when olefins are produced by a metathesis reaction wherein a composite metal oxide with plural Group 1 and Group 2 elements are contained as a co-catalyst to thereby improve in the reactivity, and methods for producing the catalyst as well as use thereof.

Description of the Related Art

Metathesis reactions of olefins are reactions whereby the same or different kind of the olefins are converted into new olefins. There are self-metathesis reactions in which, for example, two molecules of propylene are converted into ethylene and 2-butene and cross metathesis reactions in which 2-butene and 3-hexene are converted into two molecules of 2-pentenes.

When the olefin make contact with a metathesis catalyst, the reaction takes place according to a particular structural rule. This is affected by properties of raw materials supplied. This reaction is considered to take place on four central active sites in accordance with chemical equilibrium. The double bond part of olefin faces to the active site to be adsorbed and the hydrocarbon group present at one end of the double bond is exchanged, thereby proceeding the reaction. For example, in cases where of one molecule of 2-butene and ethylene is each brought into reaction, two molecules of propylene can be obtained via an exchange reaction of the hydrocarbon group. Accordingly, if that is applied to any olefin hydrocarbons, various reactions can be predicted.

Propylene is used as a raw material for a variety of industrial products and is primarily obtained from a steam reforming reaction of naphtha with various hydrocarbons, including ethylene, being generated as byproducts. Besides, propylene can be obtained via a propane dehydrogenation reaction and Fischer-Tropsch reaction; but the amount of propylene obtained is smaller than the amount obtained by the steam reforming reaction. Recently, the production of propylene by the above method cannot keep up with the demand for propylene and the production via a metathesis reaction between ethylene and 2-butene has been carried out as well.

In 1964, Phillips Corporation developed a metathesis reaction process of producing ethylene and 2-butene from propylene with a molybdenum oxide catalyst. Subsequently, what was described in Patent Document 1 or Japanese Laid Open Patent Publication No. 2008-519033 was a method employing a catalyst in which tungsten oxide was supported to silica and magnesium oxide as a co-catalyst was developed and completed as a process for propylene production by Lummus Corporation. However, the above document did not employ any composite for the co-catalyst and only showed improved propylene selectivity. There is no mention of the catalytic reactivity. Further, the metathesis catalyst disclosed by the document has a domain of promoting isomerization and thus, when a high concentration of 2-butene is used, causes 2-butene's isomerization to 1-butene. Therefore, 1-butene reacts with 2-butene or the like, thereby generating byproducts to lower the selectivity.

Further, the document describes that mixing of isomerization catalysts including magnesium oxide or the like inhibits the metathesis reaction.

Non-Patent Document 1 (Journal of Molecular Catalyst (1985, Vol. 28, Pages 117-131) reports that a tungsten oxide catalyst and magnesium oxide catalyst are mixed to be subjected to a reaction, resulting in improved activity. However, also in the above document, there is no mention of composite co-catalysts for the magnesium oxide catalyst; and the catalytic reactivity is still insufficiently described.

Patent Document 2 (Japanese Patent Publication No. 06-20556) discloses that the activity is improved by using an isomerization catalyst in which magnesium oxide and sodium are supported to γ-alumina having a large surface area and a metathesis catalyst. However, alumina includes acid points and there is a risk that these acid points cause side reactions such as generation of oligomers or the like. Further, because a catalyst with a high activity of isomerization reaction of butene is used in the metathesis reaction, when a high concentration of 2-butene is employed, 2-butene is isomerized to 1-butene and therefore 1-butene reacts with 2-butene or the like in a condition of a high conversion ratio, thereby generating byproducts to lower the selectivity.

Further, Patent Document 3 (International Laid Open Patent Publication No. WO2006/093058 Pamphlet) discloses a method of bringing a catalyst with supported Groups 1, 2, 3, or 12 metals into reaction together with a metathesis catalyst. However, the above document reports that a reaction rate is increased by having a hydrogen gas coexist and the production cost of propylene becomes high because the hydrogen gas must be used. In addition, because hydrogen is used in the reaction, propylene is hydrogenated to propane, thereby lowering the yield of propylene. Also, hydrogenation of raw materials including the hydrogenation of ethylene to ethane takes place, resulting in loss of the raw material. Further, when alumina is used as a carrier, there is a risk, similarly to the above document 2, that the acid point included in the alumina cause side reactions such as oligomers. Also still unknown is a metathesis reaction wherein a co-catalyst is made into a composite to be used.

Patent Document 4 (International Laid Open Patent Publication No. WO2010/024319 Pamphlet) discloses a method of bringing yttrium oxide or a hydrotalcite calcined product into reaction together with a metathesis catalyst. However, yttrium oxide is an expensive rare earth metal and thus there is a problem in terms of cost when yttrium oxide is used industrially. In addition, the hydrotalcite calcined product has a property of being reverted back to hydrotalcite by water; and thus problems arise in storage and practical handlings such as input to a reactor. Further, while there is disclosure with regard to the activity, no disclosure was presented on the selectivity.

PRIOR ART REFERENCES

Patent Document

Patent Document 1: Japanese Laid Open Patent Publication No. 2008-519033
Patent Document 2: Japanese Patent Publication No. 06-20556
Patent Document 3: International Laid Open Patent Publication No. WO2006/093058 Pamphlet Patent Document 4: International Laid Open Patent Publication No. WO2010/024319 Pamphlet Non-Patent Document Non-Patent Document 1: Journal of Molecular Catalyst (1985, Vol. 28, Pages 117-131)

BRIEF SUMMARY OF THE INVENTION

In a metathesis reaction, besides the main reaction, a variety of side reactions including polymerization reactions take place and thereby the active center ends up being plugged and poisoned by huge olefins, which causes lowered catalyst activity and shortens a period of regeneration cycle. Because of this, it is required to extend a reaction of activity and lower temperatures, period of regeneration cycle. Further, examples of possible side reactions besides this include isomerization reactions. For example, in a reaction of 2-butene with ethylene, examples thereof include isomerization of 2-butene to 1-butene. As this reaction progresses, properties of olefin supplied to a metathesis catalyst come to change and the reaction ends up forming unnecessary reaction products, which causes lowered catalyst selectivity.

For example, if feedstock raw materials of the olefin metathesis reaction are ethylene and 2-butene, the main product of the reaction is propylene alone. Yet, in cases where 2-butene is isomerized to 1-butene, 1-butene reacts with 2-butene to yield 2-pentene in addition to an intended product propylene. In cases where 1-butene reacts with each other, ethylene and 3-hexene are produced. Further, the produced propylene reacts with 1-butene to produce ethylene and 2-pentene. At that moment, 2-pentene and 3-hexene are considered to be non-selective products.

Because of this, what have been demanded are catalysts having a high selectivity so as not to cause polymerization reactions, isomerization from 2-butene to 1-butene, and reactions of 1-butene with other molecules, which are side reactions, and having a high activity.

In the conventional art, it has been reported that a silica catalyst with supported tungsten oxide is mixed with a magnesium oxide catalyst which is a solid base catalyst to thereby increase the activity of metathesis reaction. But, magnesium oxide which is a solid base not only increases the activity of the metathesis reaction but also exhibits an activity for isomerization reaction from 2-butene to 1-butene. In cases where 2-butene with a high concentration is employed as a feedstock raw material or in conditions for carrying out the metathesis reaction with a high activity such as a high temperature, the isomerization reaction from 2-butene to 1-butene comes to concurrently take place, which ends up decreasing the selectivity of reaction from 2-butene to propylene. Further, in catalysts that have been thus far reported, control of the strength of magnesium oxide's basicity has not been given much attention. Catalysts with a high activity of the isomerization reaction from 2-butene to 1-butene have been merely used as catalysts for the metathesis reaction and thus, when the metathesis reaction was carried out in conditions where the reaction is highly active and the 2-butene conversion ratio is increased, the amount of 1-butene produced increases as well. Further, in cases where the concentration of 2-butene was high, the amount of 1-butene produced increased as well.

What has been found this time is a catalyst that inhibits the activity of the isomerization reaction from 2-butene to 1-butene by adding Li and another kind of alkali metal to magnesium oxide to obtain a composite catalyst and to adjust the basicity, which catalyst carries out the metathesis reaction of producing propylene from 2-butene and ethylene with a high activity in an efficient fashion.

As for a catalyst used in an olefin metathesis reaction, provided is a mixed catalyst of a silica catalyst with supported tungsten oxide and magnesium oxide which is a solid base. In order to solve the above problem, the present inventors intensively studied to find that the reaction activity is markedly improved and a high propylene selectivity of at least 90% is attained by making a composite of solid base catalyst, which is a co-catalyst, from three or more kinds of basic oxides and adjusting the basicity of the surface such that the olefin metathesis reaction is promoted.

To be more specific, an important feature of the present invention is to mix to use, for a catalyst for an olefin metathesis reaction, a co-catalyst composed of three or more kinds of metal oxides as a solid base catalyst, wherein the co-catalyst has magnesium oxide and lithium as essential components, as well as alkali metals added thereto.

That is, the mixed catalyst for an olefin metathesis reaction of the present invention comprises a metathesis catalyst with tungsten oxide supported to a silica carrier and a co-catalyst that is composited from at least three oxides of Groups 1 and 2 metallic elements. That catalyst is preferably used in an olefin metathesis reaction whereby propylene is produced from ethylene and 2-butene. The above-mentioned metal oxide is preferably made by adding lithium and other alkali metals to magnesium oxide. The above-mentioned other alkali metals are preferably at least one metal selected from the group consisting of sodium, potassium, rubidium, and cesium. Further, the amount of lithium and other alkali metals supported based on the above-mentioned magnesium oxide is each preferably 0.01 to 4% by weight.

Further, the method of producing the mixed catalyst for an olefin metathesis reaction of the present invention is a method comprising mixing a co-catalyst with a metathesis catalyst which is tungsten oxide supported on a silica carrier, which co-catalyst is obtained by impregnating lithium and other alkali metals in an amount of supported metal of 0.01 to 4% by weight, respectively, based on magnesium oxide, and calcining at 400 to 700° C. in the air to form a composite oxide. Further, the method of producing propylene of the present invention is a method comprising bringing ethylene into contact with 2-butene in the presence of a mixed catalyst prepared by mixing a metathesis catalyst which is tungsten oxide supported on a silica carrier with a co-catalyst obtained by adding at least one alkali metal selected from sodium, potassium, rubidium and cesium to magnesium and lithium to form complex oxide.

The catalyst of the present invention can have a greatly improved reaction activity and exhibit a high propylene selectivity of at least 90% by making a composite of solid base catalyst, which is a co-catalyst, from three or more kinds of basic oxides to adjust the basicity of the surface such that the olefin metathesis reaction is promoted. Further, because the solid basicity can be increased to promote the metathesis reaction, the isomerization reaction from 2-butene to 1-butene was able to be inhibited to efficiently carry out only a metathesis reaction whereby propylene was produced from 2-butene and ethylene. The use of this catalyst increases the 2-butene conversion ratio, concurrently decreases the isomerization to 1-butene, and increases the propylene selectivity. Thereby, propylene can be produced at a high yield at lower temperatures to increase energy efficiency and, at the same time, side reactions in which 1-butene is involved are decreased to thereby decrease reactions, such as polymerization reactions, that cause deterioration of the activity. Therefore, it is expected to extend a period of catalyst regeneration cycle.

BRIEF DESCRIPTION OF THE SEVERAL VIEWS OF THE DRAWINGS

FIG. 1 is a graph showing the basicity of the co-catalyst of the present invention based on the desorption of carbon dioxide.

DETAILED DESCRIPTION OF THE INVENTION

Next, the present invention will be described in further detail; but the present invention is not limited thereto.

The catalyst for an olefin metathesis reaction used in the present invention comprises a metathesis catalyst and a co-catalyst. Of these, the metathesis catalyst is desirably one containing at least one kind of known metallic element such as tungsten, molybdenum, or rhenium. Among these, tungsten is most preferred. The structure of catalyst concerned may be a simple substance in a solid state whose composition include metal oxides, sulfides, chlorides, hydroxides; or may be ones in which these metal oxides, sulfides, chlorides, hydroxides or the like are immobilized onto an inorganic compound having a large surface area called a carrier. In addition, alkali metals or the like may be added. Further, the catalyst concerned is preferably in a form of oxide when used in a fixed bed flow reactor, because regeneration treatment after deterioration of the activity is carried out in the air.

Any carrier including silica, titanium oxide, and alumina can be used as long as it does not have the acidity; and preferred examples include silica. As for methods of supporting a metal to a carrier, methods known to those skilled in the art can be employed. Nitrates or hydroxides of metal and ammonium salts of poly acid and isopoly acid are used as raw materials. The carrier is impregnated with an aqueous solution thereof or sprayed with the solution to support and the resultant is calcined at a temperature of 300° C. or higher under air atmosphere, thereby obtaining the supported catalyst.

An oxides of Group 2 metal included as the co-catalyst is preferably magnesium oxide, calcium oxide, strontium oxide, and barium oxide. In particular, magnesium oxide is most preferred.

To increase the performance of the co-catalyst, it is required to make a composite co-catalyst in which two or more kinds of alkali metals are further added to the above co-catalyst. That's because the solid basicity is increased. As the metallic element capable of increasing the performance, two or more of lithium, sodium, potassium, rubidium, and cesium are used in combination to thereby improve the performance of the co-catalyst. At this time, lithium is required to be added. For example, a combination of lithium-sodium, lithium-potassium, lithium-rubidium, or lithium-cesium is preferred.

As precursors of the metallic element capable of increasing the performance of the above co-catalyst, formates, acetates, nitrates, carbonates, sulfates, chlorides, bromides, iodides, hydroxides of the above metal can be used.

As methods of adding the co-catalyst, a compact of the oxide of Group 2 metal may be impregnated with or sprayed with an aqueous solution of these precursors of the metallic element, or a powder of the oxide of Group 2 metal may be kneaded with the aqueous solution to be then formed.

This co-catalyst added with the alkali metal can be baked at 400 to 700° C. in the air to thereby obtain a composite co-catalyst. When calcination temperature is less than 400° C. the raw material of alkali metal salt would decompose insufficiently, the calcination temperature is elevated more than 700° C. the activity decreases with undesired result. At that time, the amount of metallic element in the alkali metal is preferably 0.01 to 4% by weight based on the oxide of Group 2 metal and 0.1 to 2% by weight is more preferable. If the amount is under 0.01% by weight, the effect of addition of the alkali metal is small, which is not preferred. In the alkali metal included in the co-catalyst, the weight ratio of lithium to other alkali metals is preferably 0.01 to 100. A more preferred weight ratio is 0.1 to 10. If the weight ratio of lithium to other alkali metals is less than 0.01, the production amount of 1-butene relative to the conversion ratio is increased on account of the small lithium effect. This composite co-catalyst containing lithium and other alkali metals at an appropriate ratio exhibits a high ethylene and 2-butene conversion ratio, a propylene selectivity of 90% or higher, and, in addition, a small amount of 1-butene formation; and therefore greatly contributes to the improvement of catalyst' performance.

The form of composite co-catalyst may be powders, granular forms, spherical forms, extruded molding products, or compressed tablets.

The ratio of the co-catalyst to metathesis catalyst may be any value between 0.1 and 20 in a volume ratio. If the amount of the co-catalyst is less than 0.1, the effect of increasing the activity is small because of a small amount of the co-catalyst; and if the ratio is above 20, the activity decreases due to a small amount of the metathesis catalyst, which are not preferred. Further, in cases the catalyst is filled in a fixed bed flow device, the metathesis catalyst and co-catalyst may be physically mixed to fill, or the co-catalyst and metathesis catalyst may be filled in the order mentioned from a site where is closer to the direction of supplying the raw materials.

The structure of the olefin used in the olefin metathesis reaction of the present invention is not particularly restricted; and examples of the olefin used as the raw material and the obtained olefin include propylene from ethylene and 2-butene, propylene and 1-butene from ethylene and 2-pentene, propylene and 1-pentene from ethylene and 2-hexene, propylene and isobutene from ethylene and 2-methyl-2-butene, and propylene and 3-methyl-1-butene from ethylene and 4-methyl-1-pentene. It is to be noted that the activity of the mixed catalyst for an olefin metathesis reaction is decreased by water, carbon dioxide, mercapto compounds, alcohol, or carbonyl compounds and therefore impurities in the raw material are required to be removed in advance. These removal methods can be known methods such as distillation, adsorption, extraction, and washing.

It is preferred to obtain propylene by using ethylene and 2-butene as reactant gas supplied to the metathesis catalyst and co-catalyst of the mixed catalyst for an olefin metathesis reaction of the present invention. Further, the quantity ratio of ethylene to 2-butene is preferably 1 to 5. If the ratio of ethylene to 2-butene is less than 1, an unfavorable reaction between butenes takes place; and if the ratio is above 5, a lot of energy is used for recovering unreacted ethylene, which are not preferred.

Conditions for the olefin metathesis reaction according to the present invention is a temperature of about 50 to 600° C. and preferably about 200 to 500° C. If the reaction temperature is lower than 50° C., the reaction rate decreases and the productivity of reaction products decreases; and the reaction temperature exceeds 600° C., side reactions are taken place thereby increasing byproducts and deteriorating the catalyst, which are not preferred. The reaction pressure is one atm or higher. By increasing the pressure, the reaction rate can be increased and the reaction temperature can be decreased; and 100 atm or less is usually employed by considering the reaction speed, cost for apparatus, operating cost, and the like.

When the olefin metathesis reaction of the present invention is carried out, the amount of the catalyst used is not limited.

In addition, upon carrying out the present invention, it is possible to add a solvent or gas inert to catalysts and reagents into a reaction system to carry out the invention in a diluted state. Specifically, the alkanes such as methane, ethane, propane, or butane and inert gas such as nitrogen or helium can be used as diluents. Further, any method of a batch method, semi-batch method, and continuous flow method can be employed; and the invention can be carried out in any mode of a liquid phase, gaseous phase, and gas-liquid mixed phase. From the viewpoint of reaction efficiency, the invention is preferably carried out in a gaseous phase reaction. Further, the catalyst can be carried out in a fixed bed, fluidized bed, suspension bed, shelf fixed bed, or the like.

Upon carrying out the present invention, it is desirable to dehydrate the metathesis catalyst and co-catalyst by a known method. In the case of a fixed bed reaction method, an inert gas such as nitrogen or helium is flowed in a reactor filled with the catalyst. Thereafter, in particular when tungsten and molybdenum are contained, a reducing gas such as carbon monoxide or hydrogen is flowed at a temperature of 300° C. or higher for more than 10 minutes to carry out reduction treatment; and then the inert gas can be again flowed at a temperature of 300° C. or higher for more than 10 minutes, and the catalyst is maintained at a prescribed reaction temperature. Further, plural reactors can be placed in parallel to maintain the amount of olefin produced. Further, in a fluidized bed flow reaction method and moving bed reaction method, a constant activity can be maintained by taking out a part or all of the catalysts and replenishing the equivalent amount.

The reaction product after the reaction can be separated and recovered from the catalyst by a known separation method. The olefin product can be separated by a known method such as distillation, extraction, or adsorption; and unreacted raw materials can be recovered to reuse in the reaction system.

EXAMPLES

[Performance Evaluation Method]

$WO_3/SiO_2$ catalyst as a metathesis catalyst and co-catalysts 1 to 10 prepared by a method set forth in Examples 1 to 16 and Comparative Examples 1 to 6 were physically mixed 15 mL each, in a total amount of 30 mL, in a polyethylene bag. This physically-mixed resulting product was filled in a stainless steel reactor with an inner diameter of 30 mm and a height of 400 mm, which was used as a reaction column. Further, a reactor of the same size as above was filled with 100 g of γ-alumina (NKHD-24 manufactured by Sumitomo Chemical Company, Limited) to be used as an ethylene and butene refinement column.

From the lower part of the ethylene and butene refinement column and the upper part of the reaction column, nitrogen was flowed at 630 mL/min at atmospheric pressure for 10 minutes and then hydrogen was additionally flowed at 70 mL/min. The resultant was kept at 400° C. for one hour. Thereafter, while flowing nitrogen at 300 mL/min, the ethylene and butene refinement column was kept at 50° C. and the reaction column was kept at 450° C. for one hour. Prior to the reaction, ethylene (manufactured by Takachiho Chemical Industrial Co., Ltd., purity 99.5%) at 333 mL/min from the lower part of the ethylene refinement column was mixed with trans-2-butene (manufactured by Takachiho Chemical Industrial Co., Ltd., purity 99.0%) at 167 mL/min from the lower part of the butene refinement column. The resultant was fed from the upper part of the reaction column as a mixed gas. The temperature of the reactor was set to 350 and 450° C. Further, the produced gas obtained from the lower part of the reaction column was analyzed online by gas chromatography. From the composition of reactant gas 24 hours after the beginning of the reaction, a trans-2-butene conversion ratio and propylene selectivity were determined by the equation 1 and equation 2.

$$t\text{-2-butene conversion ratio} = \frac{(\text{Change in } t\text{-2-butene concentration})}{(t\text{-2-butene concentration prior to reaction})} \times 100 \quad \text{(Equation 1)}$$

$$\text{Propylene selectivity} = \frac{(\text{Change in propylene concentration}) \times 0.5}{(\text{Change in } t\text{-2-butene concentration})} \times 100 \quad \text{(Equation 2)}$$

Comparative Example 1

A tablet of magnesium oxide in a diameter of 4.8 mm and a height of 4.8 mm was used as a co-catalyst 1. This co-catalyst was tested according to the performance evaluation method; and, as a result, the t-2-butene conversion ratio and propylene selectivity at 350° C. in regard to the mixed catalyst for an olefin metathesis reaction with the co-catalyst 1 were 20% and 99%, respectively; and the t-2-butene conversion ratio and propylene selectivity at 450° C. were found to be 67% and 98%.

Comparative Example 2

The magnesium oxide catalyst of the co-catalyst 1 used in Comparative Example 1 in an amount of 100 g was supported on an aqueous solution obtained by dissolving 9.95 g of lithium nitrate in 20 mL of water, wherein the amount of lithium supported was 1% by weight. The resultant was dried at 110° C. for one hour and baked at 600° C. in the air for two hours, thereby obtaining co-catalyst 2. When this was subjected to the performance test by the same procedures as described in Comparative Example 1, the t-2-butene conversion ratio and propylene selectivity at 350° C. in regard to the mixed catalyst for an olefin metathesis reaction using the co-catalyst 2 were 33% and 97%, respectively; and the t-2-butene conversion ratio and propylene selectivity at 450° C. were 62% and 92%.

Comparative Example 3

The magnesium oxide catalyst of the co-catalyst 1 used in Comparative Example 1 in an amount of 100 g and an aqueous solution obtained by dissolving 3.73 g of sodium nitrate in 20 mL of water were subjected to the same procedures as described in Comparative Example 2, wherein the amount of sodium supported was 1% by weight, thereby obtaining co-catalyst 3. When this was subjected to the performance test by the same procedures as described in Comparative Example 1, the t-2-butene conversion ratio and propylene selectivity at 350° C. in regard to the mixed catalyst for an olefin metathesis reaction using the co-catalyst 3 were 50% and 95%, respectively; and the t-2-butene conversion ratio and propylene selectivity at 450° C. were 70% and 93%.

Comparative Example 4

The magnesium oxide catalyst of the co-catalyst 1 used in Comparative Example 1 in an amount of 100 g and an aqueous solution obtained by dissolving 2.61 g of potassium nitrate in 20 mL of water were subjected to the same procedures as described in Comparative Example 2, wherein the amount of potassium supported was 1% by weight, thereby obtaining co-catalyst 4. When this was subjected to the performance test by the same procedures as described in Comparative Example 1, the t-2-butene conversion ratio and propylene selectivity at 350° C. in regard to the mixed catalyst for an olefin metathesis reaction using the co-catalyst 4 were 53% and 99%, respectively; and the t-2-butene conversion ratio and propylene selectivity at 450° C. were 70% and 96%.

Comparative Example 5

The magnesium oxide catalyst of the co-catalyst 1 used in Comparative Example 1 in an amount of 100 g and an aqueous solution obtained by dissolving 1.48 g of potassium nitrate in 20 mL of water were subjected to the same procedures as described in Comparative Example 2, wherein the amount of cesium supported was 1% by weight, thereby obtaining co-catalyst 5. When this was subjected to the performance test by the same procedures as described in Comparative Example 1, the t-2-butene conversion ratio and propylene selectivity at 350° C. in regard to the mixed catalyst for an olefin metathesis reaction using the co-catalyst 5 were 33% and 99%, respectively; and the t-2-butene conversion ratio and propylene selectivity at 450° C. were 65% and 97%.

Example 1

An aqueous solution prepared by dissolving 9.95 g of lithium nitrate and 3.73 g of sodium nitrate in 20 mL of water was supported on 100 g of tablet-shaped magnesium oxide, wherein the amount of lithium and sodium metals supported was each equivalent to 1% by weight. The resultant was dried at 110° C. for one hour and then baked at 600° C. in the air for two hours, thereby obtaining composite co-catalyst 6. This co-catalyst in an amount of 7.5 mL and 22.5 mL of WO₃/SiO₂ catalyst were mixed and then filled in a reactor. A test was carried out according to the performance evaluation method. As a result, the t-2-butene conversion ratio and propylene selectivity at 350° C. in regard to the mixed catalyst for an olefin metathesis reaction using the composite co-catalyst 6 were 49% and 97%, respectively; and the t-2-butene conversion ratio and propylene selectivity at 450° C. were 73% and 97%.

Example 2

An aqueous solution prepared by dissolving 9.95 g of lithium nitrate and 2.61 g of potassium nitrate, and 100 g of tablet-shaped magnesium oxide were treated by the same procedures as described in Example 1, thereby obtaining composite co-catalyst 7, wherein the amount of lithium and potassium metals supported was each equivalent to 1% by weight. When this was subjected to the performance test by the same procedures as described in Example 1, the t-2-butene conversion ratio and propylene selectivity at 350° C. in regard to the mixed catalyst for an olefin metathesis reaction using the composite co-catalyst 7 were 74% and 95%, respectively; and the t-2-butene conversion ratio and propylene selectivity at 450° C. were 78% and 96%. Further, the t-2-butene conversion ratio and propylene selectivity at 300° C. were 58% and 97%.

Example 3

An aqueous solution prepared by dissolving 9.95 g of lithium nitrate and 1.74 g of rubidium nitrate, and 100 g of tablet-shaped magnesium oxide catalyst were treated by the same procedures as described in Example 1, thereby obtaining composite co-catalyst 8, wherein the amount of lithium and rubidium metals supported was each equivalent to 1% by weight. When this was subjected to the performance test by the same procedures as described in Example 1, the t-2-butene conversion ratio and propylene selectivity at 350° C. in regard to the mixed catalyst for an olefin metathesis reaction using the composite co-catalyst 8 were 46% and 94%, respectively; and the t-2-butene conversion ratio and propylene selectivity at 450° C. were 75% and 94%.

Example 4

An aqueous solution prepared by dissolving 9.95 g of lithium nitrate and 1.48 g of cesium nitrate, and 100 g of tablet-shaped magnesium oxide catalyst were treated by the same procedures as described in Example 1, thereby obtaining composite co-catalyst 9, wherein the amount of lithium and cesium metals supported was each equivalent to 1% by weight. When this was subjected to the performance test by the same procedures as described in Example 1, the t-2-butene conversion ratio and propylene selectivity at 350° C. in regard to the mixed catalyst for an olefin metathesis reaction using the composite co-catalyst 9 were 56% and 93%, respectively; and the t-2-butene conversion ratio and propylene selectivity at 450° C. were 74% and 93%.

Comparative Example 6

An aqueous solution prepared by dissolving 1.76 g of sodium nitrate and 1.48 g of potassium nitrate, and 100 g of tablet-shaped magnesium oxide catalyst were treated by the same procedures as described in Example 1, thereby obtaining co-catalyst 10, wherein the amount of each metal supported was each equivalent to 1% by weight. When this was subjected to the performance test by the same procedures as described in Example 1, the t-2-butene conversion ratio and propylene selectivity at 350° C. in regard to the mixed catalyst for an olefin metathesis reaction using the co-catalyst 10 were 32% and 99%, respectively; and the t-2-butene conversion ratio and propylene selectivity at 450° C. were 58% and 97%.

TABLE 1

Results of Performance Evaluation

| Co-catalyst | Metal added | Ethylene conversion ratio (%) | 2-butene conversion ratio (%) | Propylene selectivity (%) | Amount of 1-butene produced (%) |
|---|---|---|---|---|---|
| Performance at 450° C. | | | | | |
| 1 (Comparative Example 1) | None | 21 | 67 | 98 | 1.9 |
| 2 (Comparative Example 2) | Li | 18 | 62 | 92 | 4.2 |
| 3 (Comparative Example 3) | Na | 20 | 70 | 93 | 8.5 |
| 4 (Comparative Example 4) | K | 21 | 70 | 96 | 8.8 |
| 5 (Comparative Example 5) | Cs | 20 | 65 | 97 | 3.9 |
| 6 (Example 1) | Li/Na | 32 | 73 | 97 | 1.2 |
| 7 (Example 2) | Li/K | 35 | 78 | 96 | 3.8 |
| 8 (Example 3) | Li/Rb | 31 | 75 | 94 | 1.1 |
| 9 (Example 4) | Li/Cs | 32 | 74 | 93 | 1.3 |
| 10 (Comparative Example 6) | Na/K | 22 | 58 | 97 | 1.7 |
| Performance at 350° C. | | | | | |
| 1 (Comparative Example 1) | None | 3 | 20 | 99 | 0.9 |
| 2 (Comparative Example 2) | Li | 8 | 33 | 97 | 0.9 |
| 3 (Comparative Example 3) | Na | 13 | 50 | 95 | 5.8 |
| 4 (Comparative Example 4) | K | 15 | 53 | 99 | 8.4 |
| 5 (Comparative Example 5) | Cs | 9 | 33 | 99 | 3.4 |
| 6 (Example 1) | Li/Na | 22 | 49 | 97 | 0.7 |
| 7 (Example 2) | Li/K | 30 | 74 | 95 | 2.2 |
| 8 (Example 3) | Li/Rb | 20 | 46 | 94 | 0.6 |
| 9 (Example 4) | Li/Cs | 24 | 56 | 93 | 0.6 |
| 10 (Comparative Example 6) | Na/K | 12 | 32 | 99 | 0.7 |

Table 1 above summarizes the test results of the performance evaluation of the mixed catalyst for an olefin metathesis reaction using co-catalysts 1 to 10. Table 1 reveals that the catalysts using the co-catalysts 6 to 9 in which two kinds of metals are supported in conjunction with magnesium oxide exhibit improved 2-butene conversion ratio and ethylene conversion ratio as compared with the catalysts using the co-catalysts 1 to 5 without added metals or only with one kind of them. In particular, the ethylene conversion ratio significantly improved to greatly improve the reaction activity. It becomes clear at the same time that even at high temperatures at which the conversion ratio is high, the propylene selectivity was able to be maintained at the same level and the efficiency of propylene production was greatly improved. Also, the amount of 1-butene produced is, in spite of a high ethylene and 2-butene conversion ratio, a lower value than that in Comparative Examples, indicating that the selectivity is high. Further, in cases, including the co-catalyst 10, where a combination of two kinds of alkali metals other than lithium is selected to use in the catalyst, the 2-butene conversion ratio is further lower and the reaction activity greatly decreases, as compared with the catalysts using the co-catalysts 1 to 5 with one kind of alkali metal or the catalyst without using any alkali metal, implying that lithium must be necessarily contained as the co-catalyst. In particular, the co-catalyst 7 exhibited the equivalent activity at a reaction temperature of 350° C. and 450° C., and also a high selectivity. On the top of that, when the reaction was carried out at 300° C., the ethylene conversion ratio was found to be 27%; the 2-butene conversion ratio was 58%; the propylene selectivity was 97%; and the amount of 1-butene produced was 1.2%. The co-catalyst 7 showed a compatible or better activity and selectivity even at a reaction temperature that is 50 degrees lower than the co-catalysts 1 to 5 and 10.

Example 5

<Li/K=0.01>

An aqueous solution prepared by dissolving 0.09 g of lithium nitrate and 2.61 g of potassium nitrate, and 100 g of tablet-shaped magnesium oxide catalyst were treated by the same procedures as described in Example 1, thereby obtaining co-catalyst 11, wherein the amount of lithium supported was equivalent to 0.01% by weight and the amount of potassium supported was equivalent to 1% by weight. When this was subjected to the performance test by the same procedures as described in Example 1, the t-2-butene conversion ratio and propylene selectivity at 350° C. in regard to the mixed catalyst for an olefin metathesis reaction using the co-catalyst 11 were 43% and 98%, respectively; and the t-2-butene conversion ratio and propylene selectivity at 450° C. were 67% and 96%.

Example 6

Li/K=0.1

An aqueous solution prepared by dissolving 0.99 g of lithium nitrate and 2.61 g of potassium nitrate, and 100 g of tablet-shaped magnesium oxide catalyst were treated by the same procedures as described in Example 1, thereby obtaining co-catalyst 12, wherein the amount of lithium supported was equivalent to 0.1% by weight and the amount of potassium supported was equivalent to 1% by weight. When this was subjected to the performance test by the same procedures as described in Example 1, the t-2-butene conversion ratio and propylene selectivity at 350° C. in regard to the mixed catalyst for an olefin metathesis reaction using the co-catalyst 12 were 65% and 98%, respectively; and the t-2-butene conversion ratio and propylene selectivity at 450° C. were 75% and 98%.

Example 7

Li/K=0.5

An aqueous solution prepared by dissolving 9.95 g of lithium nitrate and 5.22 g of potassium nitrate, and 100 g of tablet-shaped magnesium oxide catalyst were treated by the same procedures as described in Example 1, thereby obtaining co-catalyst 13, wherein the amount of lithium supported was equivalent to 1% by weight and the amount of potassium supported was equivalent to 2% by weight. When this was subjected to the performance test by the same procedures as described in Example 1, the t-2-butene conversion ratio and propylene selectivity at 350° C. in regard to the mixed catalyst for an olefin metathesis reaction using the co-catalyst 13 were 68% and 98%, respectively; and the t-2-butene conversion ratio and propylene selectivity at 450° C. were 75% and 98%.

Example 8

Li/K=2

An aqueous solution prepared by dissolving 19.90 g of lithium nitrate and 2.61 g of potassium nitrate, and 100 g of tablet-shaped magnesium oxide catalyst were treated by the same procedures as described in Example 1, thereby obtaining co-catalyst 14, wherein the amount of lithium supported was equivalent to 2% by weight and the amount of potassium supported was equivalent to 1% by weight. When this was subjected to the performance test by the same procedures as described in Example 1, the t-2-butene conversion ratio and propylene selectivity at 350° C. in regard to the mixed catalyst for an olefin metathesis reaction using the co-catalyst 14 were 69% and 98%, respectively; and the t-2-butene conversion ratio and propylene selectivity at 450° C. were 71% and 98%.

Example 9

Li/K=10

An aqueous solution prepared by dissolving 9.95 g of lithium nitrate and 0.26 g of potassium nitrate, and 100 g of tablet-shaped magnesium oxide catalyst were treated by the same procedures as described in Example, thereby obtaining co-catalyst 15, wherein the amount of lithium supported was equivalent to 1% by weight and the amount of potassium supported was equivalent to 0.1% by weight. When this was subjected to the performance test by the same procedures as described in Example 1, the t-2-butene conversion ratio and propylene selectivity at 350° C. in regard to the mixed catalyst for an olefin metathesis reaction using the co-catalyst 15 were 72% and 99%, respectively; and the t-2-butene conversion ratio and propylene selectivity at 450° C. were 76% and 98%.

Example 10

Li/K=100

An aqueous solution prepared by dissolving 9.95 g of lithium nitrate and 0.03 g of potassium nitrate, and 100 g of tablet-shaped magnesium oxide catalyst were treated by the same procedures as described in Example 1, thereby obtaining co-catalyst 16, wherein the amount of lithium supported was equivalent to 1% by weight and the amount of potassium supported was equivalent to 0.01% by weight. When this was subjected to the performance test by the same procedures as described in Example 1, the t-2-butene conversion ratio and propylene selectivity at 350° C. in regard to the mixed catalyst for an olefin metathesis reaction using the co-catalyst 16 were 44% and 99%, respectively; and the t-2-butene conversion ratio and propylene selectivity at 450° C. were 69% and 99%.

Table 2 below summarizes the test results of the performance evaluation of mixed catalyst for an olefin metathesis reaction using the co-catalysts 7 and 11 to 16 in which the content of lithium and potassium with supported magnesium oxide was changed. As comparison, shown are the results of the performance evaluation of mixed catalyst for an olefin metathesis reaction using the co-catalyst 2 containing potassium alone with no lithium to magnesium oxide and the co-catalyst 4 containing lithium alone to magnesium oxide. From these results, when lithium alone or potassium alone is used as the added metal to magnesium oxide in the co-catalyst and the olefin metathesis reaction is carried out in the presence of the mixed catalyst for an olefin metathesis reaction at a temperature of both 350° C. and 450° C., the ethylene conversion ratio and 2-butene conversion ratio are low and, in addition, the amount of 1-butene produced is large. On the other hand, when lithium and potassium are added in combination as co-catalysts, the ethylene conversion ratio, 2-butene conversion ratio, and propylene selectivity greatly increase and the amount of 1-butene produced decreases at both temperatures. In particular, it was found that when the Li/K ratio in the co-catalyst was 0.1 to 10 at a lower temperature of 350° C., both of the 2-butene conversion ratio and propylene selectivity using the mixed catalyst for an olefin metathesis reaction containing such a co-catalyst come to very high values and the amount of 1-butene produced was low for the activity, thereby indicating a high reaction activity and low side reactions.

TABLE 2

Results of Performance Evaluation

| | | | | Performance at 450° C. | | | |
|---|---|---|---|---|---|---|---|
| Co-catalyst | Li (% by weight) | K (% by weight) | Li/K ratio | Ethylene conversion ratio (%) | 2-butene conversion ratio (%) | Propylene selectivity (%) | Amount of 1-butene produced (%) |
| 4 (Comparative Example 4) | 0 | 1 | — | 21 | 70 | 96 | 8.8 |
| 11 (Example 5) | 0.01 | 1 | 0.01 | 22 | 67 | 96 | 1.4 |
| 12 (Example 6) | 0.1 | 1 | 0.1 | 21 | 75 | 98 | 1.2 |
| 13 (Example 7) | 1 | 2 | 0.5 | 28 | 75 | 98 | 1.4 |
| 7 (Example 2) | 1 | 1 | 1 | 35 | 78 | 96 | 3.8 |
| 14 (Example 8) | 2 | 1 | 2 | 36 | 71 | 98 | 1.2 |
| 15 (Example 9) | 1 | 0.1 | 10 | 34 | 76 | 98 | 1.1 |
| 16 (Example 10) | 1 | 0.01 | 100 | 23 | 69 | 99 | 0.9 |
| 2 (Comparative Example 2) | 1 | 0 | — | 18 | 62 | 92 | 4.2 |

| | | | | Performance at 350° C. | | | |
|---|---|---|---|---|---|---|---|
| Co-catalyst | Li (% by weight) | K (% by weight) | Li/K ratio | Ethylene conversion ratio (%) | 2-butene conversion ratio (%) | Propylene selectivity (%) | Amount of 1-butene produced (%) |
| 4 (Comparative Example 4) | 0 | 1 | — | 15 | 53 | 99 | 8.4 |
| 11 (Example 5) | 0.01 | 1 | 0.01 | 8 | 43 | 98 | 0.5 |
| 12 (Example 6) | 0.1 | 1 | 0.1 | 19 | 65 | 98 | 0.5 |

TABLE 2-continued

Results of Performance Evaluation

| | | | | | | | |
|---|---|---|---|---|---|---|---|
| 13 (Example 7) | 1 | 2 | 0.5 | 26 | 68 | 98 | 0.6 |
| 7 (Example 2) | 1 | 1 | 1 | 30 | 74 | 95 | 2.2 |
| 14 (Example 8) | 2 | 1 | 2 | 35 | 69 | 98 | 0.3 |
| 15 (Example 9) | 1 | 0.1 | 10 | 34 | 72 | 99 | 0.2 |
| 16 (Example 10) | 1 | 0.01 | 100 | 10 | 44 | 99 | 0.2 |
| 2 (Comparative Example 2) | 1 | 0 | — | 8 | 33 | 97 | 0.9 |

Further, the basicity of the metathesis co-catalyst itself was evaluated by desorption of carbon dioxide (temperature programmed desorption: TPD). The measurement was carried out by making the catalyst adsorb carbon dioxide as a probe molecule and determining the amount of carbon dioxide desorbed when the temperature of the catalyst layer was continuously increased and the desorption temperature. Carbon dioxide adsorbed at a weak base point is desorbed at low temperatures and carbon dioxide adsorbed at a strong base point is desorbed at high temperatures. The results are shown in FIG. 1. The vertical axis represents the ionic strength and the horizontal axis represents the temperature. The co-catalyst 1 of Comparative Example 1 (indicated by MgO) exhibited peaks of carbon dioxide desorption around 200° C. and 600° C. The co-catalyst 2 with supported lithium of Comparative Example 2 (indicated by Li/MgO) had attenuated desorption peak around 200° C. and exhibited new desorption peaks around 400° C. and 600° C. Further, the co-catalyst 4 supporting potassium of Comparative Example 4 (indicated by K/MgO) exhibited a desorption peak around 200° C. and a desorption peak around 600° C. In contrast to this, the co-catalyst 7 with supported lithium and potassium of Example 2 (Li—K/MgO) exhibits a desorption peak only around 400° C. The peak was not a peak obtained by simply summing the peak of the co-catalyst 4 with supported potassium and the peak of the co-catalyst 2 with supported lithium. It is thought that a reaction of magnesium oxide with lithium and potassium resulted in generating a new base point on the catalyst surface. Thereby, it is presumed that a high selectivity and low production of side reaction products are attained by making a composite with lithium and other alkali metals, in particular, potassium in the co-catalyst to change the base point of the catalyst surface, eliciting maximally the activity of metathesis reaction of ethylene and 2-butene alone without isomerization reaction of 2-butene, and thus reacting quantitatively these two reactants at a ratio of one to one in an efficient fashion.

As afore described, by combination of co-catalyst for use in the mixed catalyst for olefin metathesis with two or more metals, a base point of the surface as a whole of the mixed catalyst for olefin metathesis is controlled and the reacting as a whole at a low temperature could be enhanced. There was a concern that an enhancement of the reactivity might cause the progression of side reactions. But it was possible to make the metathesis co-catalyst of a high propylene selectivity of 95% or more at 350° C. and exhibited a low amount of 1-butene formation of 2.2% or less despite of having a high ethylene conversion ratio and a high 2-butene conversion ratio, and the lithium composite could produce a metathesis co-catalyst of higher activity as compared with the conventional catalyst.

According to the invention, a composite co-catalyst may control a basicity of the surface of the catalyst. Therefore, without taking the purity of raw materials into consideration as conventionally worked, the reaction activity and the selectivity could be simply enhanced. Further, despite of high reaction activity at the low temperatures, the productivity of propylene at a law temperature could be enhanced, which is very advantageous from the viewpoint of industrial production, safety, and costs.

What is claimed is:

1. A mixed catalyst for an olefin metathesis reaction, comprising a metathesis catalyst which is tungsten oxide supported on a silica carrier and a co-catalyst which is a complex oxide comprising magnesium oxide, lithium and at least one other alkali metal, wherein said lithium and said at least one other alkali metal are supported in an amount of supported metal of 0.01 to 4% by weight, respectively, based on said magnesium oxide and the weight ratio of said lithium to said at least one other alkali metal is 0.1 to 10, and wherein the ratio of the co-catalyst to the metathesis catalyst is 0.1 to 20 in a volume ratio, and wherein the complex oxide comprises a combination of lithium-sodium, lithium-potassium, lithium-rubidium or lithium-cesium.

2. The mixed catalyst for an olefin metathesis reaction according to claim 1, which is used in an olefin metathesis reaction whereby propylene is generated from ethylene and 2-butene.

3. A method of producing a mixed catalyst for an olefin metathesis reaction comprising mixing a co-catalyst with a metathesis catalyst which is tungsten oxide supported on a silica carrier, which co-catalyst is a complex oxide obtained by impregnating magnesium oxide with lithium and at least one other alkali metal, wherein said lithium and said at least one other alkali metal are supported in an amount of supported metal of 0.01 to 4% by weight, respectively, based on said magnesium oxide, wherein the weight ratio of said lithium to said at least one other alkali metal is 0.1 to 10, the ratio of the co-catalyst to the metathesis catalyst is 0.1 to 20 in a volume ratio, and the complex oxide comprises a combination of lithium-sodium, lithium-potassium, lithium-rubidium or lithium-cesium, and sintering at 400° C. to 700° C. in the air to form a composite oxide.

4. A method of producing propylene comprising reaction of ethylene and 2-butene in the presence of an olefin metathesis catalyst prepared by mixing tungsten oxide supported on a silica carrier and co-catalyst obtained by adding at least one other alkali metal selected from sodium, potassium, rubidium, and cesium to magnesium oxide and lithium to form a complex oxide, wherein said lithium and said at least one other alkali metal are supported in an amount of supported metal of 0.01 to 4% by weight, respectively, based on said magnesium oxide, wherein the weight ratio of said lithium to said at least one other alkali metal is 0.1 to 10 and the ratio of the co-catalyst to the metathesis catalyst is 0.1 to 20 in a volume ratio.

* * * * *